US010169881B2

(12) United States Patent
Karasawa

(10) Patent No.: US 10,169,881 B2
(45) Date of Patent: Jan. 1, 2019

(54) ANALYSIS DEVICE, SYSTEM AND PROGRAM

(71) Applicant: 3M INNOVATIVE PROPERTIES COMPANY, St. Paul, MN (US)

(72) Inventor: Fumio Karasawa, Tokyo (JP)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 151 days.

(21) Appl. No.: 15/106,203

(22) PCT Filed: Dec. 22, 2014

(86) PCT No.: PCT/US2014/071815
§ 371 (c)(1),
(2) Date: Jun. 17, 2016

(87) PCT Pub. No.: WO2015/100208
PCT Pub. Date: Jul. 2, 2015

(65) Prior Publication Data
US 2016/0321824 A1 Nov. 3, 2016

(30) Foreign Application Priority Data

Dec. 27, 2013 (JP) ................. 2013-273475

(51) Int. Cl.
*H04N 7/18* (2006.01)
*G06T 7/40* (2017.01)
(Continued)

(52) U.S. Cl.
CPC ............. *G06T 7/408* (2013.01); *G01N 21/78* (2013.01); *G01N 21/80* (2013.01);
(Continued)

(58) Field of Classification Search
CPC ........... H04N 5/232; G06T 7/408; G06T 7/90; G06T 2207/10024; G01N 21/78; G01N 21/8483; G01N 21/274; G01N 33/03
(Continued)

(56) References Cited

U.S. PATENT DOCUMENTS 4,654,309 A 3/1987 Mlinar et al.
5,565,990 A 10/1996 Hosoi
(Continued)

FOREIGN PATENT DOCUMENTS

EP 0711999 5/1996
JP 63-229335 9/1988
(Continued)

OTHER PUBLICATIONS

Standard of the Camera & Imaging Products Association, CIPS DC-004-Translation—2004, 31 pages.
(Continued)

*Primary Examiner* — Michael Lee
(74) *Attorney, Agent, or Firm* — X. Christina Huang

(57) ABSTRACT

A general purpose device, system, and program perform colorimetric analysis by automatically comparing the color of an object to be analyzed with reference information. The device includes an imaging unit that takes images of the object to be analyzed; a memory unit that stores reference information of color information of the object in accordance with properties of the object; a conversion unit that makes the color space of the image data and the color space of the reference information the same by converting the color spaces when the color space of the image data of the object and the color space of the reference information are different; a determination unit that determines the properties of the object by comparing the color information of the image data and the color information of the reference information (Continued)

in a common color space; and a display unit that displays the determination results.

11 Claims, 9 Drawing Sheets

(51) Int. Cl.
    *G01N 21/84*      (2006.01)
    *G01N 21/78*      (2006.01)
    *H04N 5/232*      (2006.01)
    *G06T 7/90*      (2017.01)
    *G01N 21/80*      (2006.01)
    *G01N 33/03*      (2006.01)
    *G01N 21/27*      (2006.01)

(52) U.S. Cl.
    CPC .......... *G01N 21/8483* (2013.01); *G06T 7/90* (2017.01); *H04N 5/232* (2013.01); *G01N 21/274* (2013.01); *G01N 33/03* (2013.01); *G06T 2207/10024* (2013.01)

(58) Field of Classification Search
    USPC .......................................................... 348/135
    See application file for complete search history.

(56) References Cited

U.S. PATENT DOCUMENTS

| | | |
|---|---|---|
| 5,786,223 A | 7/1998 | Terashima |
| 6,198,552 B1 | 3/2001 | Nagae |
| 6,295,506 B1 | 9/2001 | Heinonen et al. |
| 8,463,119 B2 | 6/2013 | Kubota |
| 2006/0067668 A1 | 3/2006 | Kita |
| 2006/0098108 A1 | 5/2006 | Kurosawa |
| 2006/0262659 A1 | 11/2006 | Kurosawa |
| 2007/0013927 A1* | 1/2007 | Miyahara ............. H04N 1/6058 358/1.9 |
| 2008/0107332 A1* | 5/2008 | Nishikuni ............. H04N 1/603 382/166 |
| 2008/0187217 A1* | 8/2008 | Okutsu ................ G06K 9/4652 382/165 |
| 2012/0063652 A1 | 3/2012 | Chen et al. |
| 2013/0154903 A1* | 6/2013 | Kim ........................ G09G 5/02 345/1.1 |
| 2013/0308852 A1 | 11/2013 | Hamsici |
| 2015/0348245 A1* | 12/2015 | Horiuchi ................ G06T 5/005 382/167 |

FOREIGN PATENT DOCUMENTS

| | | |
|---|---|---|
| JP | 1-174966 | 7/1989 |
| JP | 6-242487 | 9/1994 |
| JP | 2003-9163 | 1/2003 |
| JP | 2005-33434 | 2/2005 |
| JP | 2006-33159 | 2/2006 |
| JP | 2007-285988 A | 11/2007 |
| JP | 2009-53063 | 3/2009 |
| JP | 2010-281610 | 12/2010 |
| WO | WO 00/04492 A2 | 1/2000 |
| WO | WO 2008-077015 | 6/2008 |
| WO | WO 2013-010178 | 1/2013 |
| WO | WO 2013-116831 | 8/2013 |

OTHER PUBLICATIONS

International Search Report for PCT International Application No. PCT/US 14/71815 dated Sep. 2, 2015, 3 pages.

* cited by examiner

ANALYSIS DEVICE, SYSTEM AND PROGRAM

This application claims the benefit of Japan Application No. 2013-273475, filed Dec. 27, 2013, the entire content of which being incorporated herein by reference.

TECHNICAL FIELD

The present disclosure relates to an analysis device, system, and program.

BACKGROUND

Patent Document 1 discloses a method to determine the degree of degradation of a fat by oxidation by mixing and agitating the fat being tested with a reagent, and measuring the degree of coloration caused by the reaction between the fat oxide in the fat being tested and the reagent.

Also, Patent Document 2 discloses a fat degradation measuring device that determines the degree of degradation of fat by irradiating light onto a coloring unit in which different colors are produced in accordance with the degree of degradation of the fat that has reacted, receiving the light reflected by the coloring unit, determining the degree of degradation of the fat based on information on the strength of the reflected light and comparative information, and displaying the degree of degradation.

PRIOR ART DOCUMENTS

Patent Documents

Patent Document 1: Japanese Unexamined Patent Application Publication No. H01-174966
Patent Document 2: Japanese Unexamined Patent Application Publication No. 2010-281610

SUMMARY

At present, when carrying out colorimetric analysis, a test specimen that includes a coloring agent is mainly used as it is easier to handle than a liquid reagent as in Patent Document 1. In colorimetric analysis using a test specimen, the color of the test specimen that has been changed by reaction with the object to be analyzed and colors on a reference table are compared, to determine the properties of the object to be analyzed. However, if this color comparison is carried out by a person, there is the problem that the determination results are subjective.

In the case of a measuring device that automatically reads and compares the color of the test specimen and displays the result as a numeral, as in Patent Document 2, it is possible to carry out objective colorimetric analysis. However, to carry out objective measurement expensive dedicated measuring equipment must be used, which also requires maintenance work. Therefore a low cost general purpose device that can easily carry out colorimetric analysis is desirable.

Therefore, it is an object of the present disclosure to enable colorimetric analysis that automatically compares the color of an object being analyzed with reference information, using a general purpose device.

Means to Solve the Problem

The device according to the present disclosure is a device for performing colorimetric analysis and includes an imaging unit that takes images of an object to be analyzed; a memory unit that stores reference information of color information of the object to be analyzed in accordance with the properties of the object to be analyzed; a conversion unit that makes the color space of the image data and the color space of the reference information the same by converting at least one of the color spaces when the color space of the image data of the object to be analyzed taken by the imaging unit and the color space of the reference information are different; a determination unit that determines the properties of the object to be analyzed by comparing the color information of the image data and the color information of the reference information in a common color space; and a display unit that displays the determination results of the determination unit.

In the above device, preferably when the color space of the image data and the color space of the reference information are different, the conversion unit converts the color information of the reference information to values of color information in the color space of the image data.

In the above device, preferably when the color space of the image data and the color space of the reference information are different, the conversion unit converts the color information of the image data to values of color information in the color space of the reference information.

In the above device, preferably when the color space of the image data and the color space of the reference information are different, the conversion unit converts the color information of the color space of the image data and the color information of the color space of the reference information into values of color information of a common color space.

In the above device, preferably the reference information is prepared in advance using image data taken by the imaging unit of the object to be analyzed having different known properties.

In the above device, preferably the reference information is prepared in advance using image data taken by an imaging device that is different from the imaging unit of the object to be analyzed having different known properties.

In the above device, preferably the reference information is prepared by obtaining in advance the optical spectra of the object to be analyzed with known properties, and converting color information calculated from the optical spectra into color information in the color space of the image data.

In the above device, preferably the imaging unit takes an image of a test specimen that has contacted the object to be analyzed, and the memory unit stores as reference information color information indicating the color of the test specimen in accordance with the properties of the object to be analyzed.

In the above device, preferably the object to be analyzed is a liquid, the imaging unit takes an image of a test specimen soaked with the liquid to be analyzed, and the memory unit stores as reference information color information representing the color of the test specimen in accordance with the properties of the liquid.

Preferably the above device further includes a degree of contamination correction unit that determines the degree of contamination of the liquid based on the color of the test specimen soaked with the liquid, and applies a correction that is predetermined in accordance with the degree of contamination to the value converted by the conversion unit, and the determination unit compares the value corrected by the degree of contamination correction unit with the reference information.

Preferably the above device further includes a light source correction unit that calculates the color temperature of the light source based on the whole or a part of the image data of the image taken by the imaging unit, and applies a correction in accordance with the color temperature to the value converted by the conversion unit, and the determination unit compares the value corrected by the light source correction unit with the reference information.

Preferably the above device further includes a light exposure correction unit that calculates the light exposure conditions of the light source based on the whole or a part of the image data of the image taken by the imaging unit, and applies a correction in accordance with the light exposure conditions to the value converted by the conversion unit, and the determination unit compares the value corrected by the light exposure correction unit with the reference information.

In the above device, preferably the determination unit determines the properties of the object to be analyzed by comparing the values of the color information in the common color space for a plurality of points in the image taken by the imaging unit with the reference information.

The system according to the present disclosure is a system that carries out colorimetric analysis and that includes a terminal device and a server that can communicate with each other, the terminal device includes an imaging unit that takes images of an object to be analyzed, a terminal communication unit that transmits image data of the object to be analyzed taken by the imaging unit to the server, and receives determination results for the image data from the server, and a display unit that displays the determination results; and the server includes a memory unit that stores reference information of color information of the object to be analyzed in accordance with the properties of the object to be analyzed, a conversion unit that, when the color space of the image data of the object to be analyzed received from the terminal device and the color space of the reference information are different, makes the color space of the image data and the color space of the reference information the same by converting at least one of the color spaces, a determination unit that determines the properties of the object to be analyzed by comparing the color information of the image data and the color information of the reference information in a common color space, and a server communication unit that receives the image data from the terminal device and transmits the determination results to the terminal device.

The program according to the present disclosure is executed on a computer that includes a memory unit that stores reference information of color information of an object to be analyzed in accordance with the properties of the object to be analyzed, and the program includes: acquiring image data of the object to be analyzed taken by an imaging unit; making the color space of the image data and the color space of the reference information the same by converting at least one of the color spaces when the color space of the image data of the object to be analyzed taken by the imaging device and the color space of the reference information are different; determining the properties of the object to be analyzed by comparing the color information of the image data and the color information of the reference information in a common color space; and preparing display data for displaying the determination results of the properties of the object to be analyzed.

DETAILED DESCRIPTION

The following is a detailed description of the device, system, and program according to the present disclosure, with reference to the drawings. However, please note that the technical scope of the present disclosure is not limited to these embodiments, but the technical scope extends to the invention as disclosed in the scope of the patent claims and their equivalents.

Figure 1:
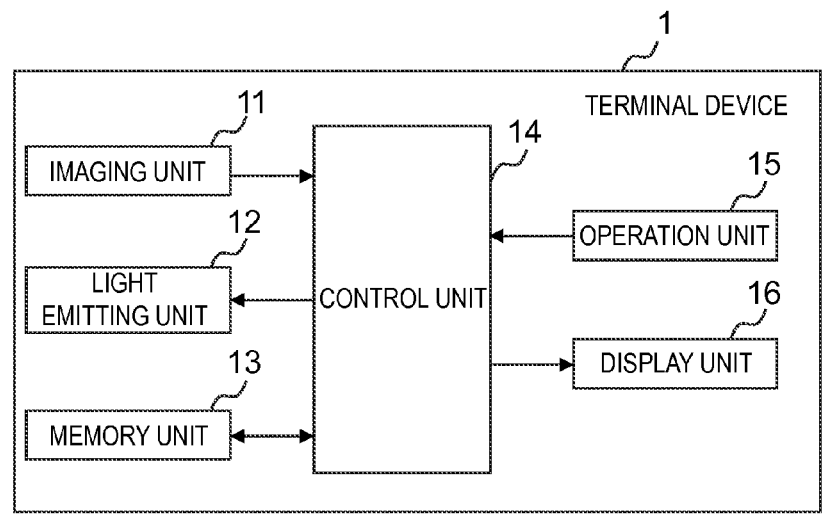
FIG. 1 is a schematic configuration of one embodiment of a terminal device 1.

FIG. 1 is a schematic configuration of one embodiment of a terminal device 1. The terminal device 1 includes an imaging unit 11, a light emitting unit 12, a memory unit 13, a control unit 14, an operation unit 15, and a display unit 16.

The terminal device 1 is an example of device for performing colorimetric analysis, for example, a mobile terminal such as a smart phone or the like, that includes a camera. The object to be analyzed is, for example, cooking oil, or a liquid such as factory effluent, or the like. The terminal device 1 takes an image of a test specimen that is soaked with the object to be analyzed, and the properties of the object to be analyzed are determined based on the color of the test specimen. These properties can include, for example, the degree of oxidation, pH, the quantity of specific inorganic or organic substances, and so on. In the following, an example is described in which the object to be analyzed is cooking oil, and the property of the object to be analyzed is measurement of the degree of oxidation of the cooking oil.

The imaging unit 11 takes an image of the test specimen that contacts the object to be analyzed, and obtains image data in the format of RAW (DNG) data, JPEG (JFIF) data, or RGB data, or the like. Any one of these data formats may be used, but in the following an example is described in which the imaging unit 11 acquires JPEG (JFIF) data. The light emitting unit 12 is disposed adjacent to a lens on the imaging unit 11, and if necessary it emits light when an image is being taken by the imaging unit 11.

The memory unit 13 is, for example, a semiconductor memory that stores the image data taken by the imaging unit 11, data necessary for operation of the terminal unit 1, and so on. Also, the memory unit 13 stores color information of the object to be analyzed in accordance with the property (for example, the degree of oxidation of the cooking oil) of the object to be analyzed, as reference information. This reference information corresponds to, for example, so-called acid values (AV values) that indicate the degree of oxidation, and sRGB data that indicate the color of the test specimen soaked with cooking oil of that degree of oxidation.

The control unit 14 includes a CPU, RAM, ROM, and so on, and controls the operation of the terminal device 1. The operation unit 15 includes, for example, a touch panel, a keyboard, or the like, and receives operations from a user. The display unit 16 is, for example, a liquid crystal display, and may be integrated with the operation unit 15 as a touch panel display. The display unit 16 displays the results of the object to be analyzed determined by the control unit 14.

Figure 2:
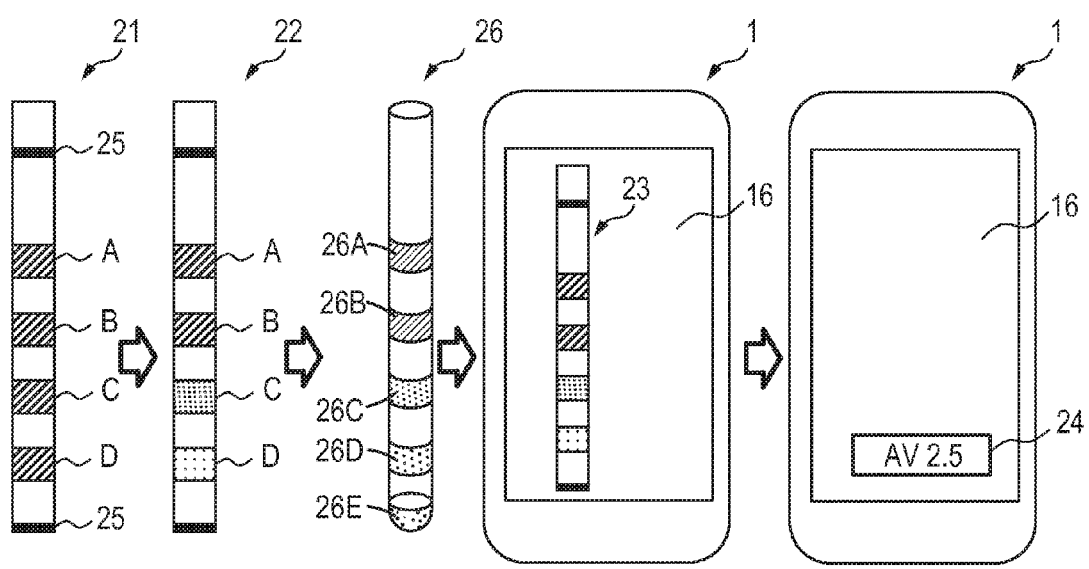
FIG. 2 is an explanatory view explaining measurement by the terminal device 1 using a test specimen.

FIG. 2 is an explanatory view explaining measurement by the terminal device 1 using a test specimen. In FIG. 2, a test specimen 21, a test specimen 22 soaked with the cooking oil that is the object to be analyzed, and a test specimen 26 includes a tube containing liquid for testing with a reference chart, and the terminal device 1 displaying an image 23 of the test specimen 22 are shown.

The test specimen 21 includes a band A, a band B, a band C, and a band D that are areas where the color changes after reaction with the object to be analyzed. Also, the test specimen 21 includes marks 25 for image recognition provided one each on the top portion and on the bottom portion. Band A to band D are, for example, the same blue color when there is no reaction with the object to be analyzed, and the areas other than band A to band D on the test specimen 21 are white.

When the test specimen 21 is soaked with the cooking oil that is the object to be analyzed, the color of band A to band D changes from, for example, blue to yellow, in accordance with the degree of oxidation. In this case, if the degree of oxidation is low only band D changes color, but as the degree of oxidation increases, more areas change color in the order band D, band C, band B, band A, and if the degree of oxidation is high, all areas change color. In FIG. 2, a test specimen 22 in which band C and band D have changed color is shown.

The test specimen 26 is a tube including reference color bands 26A, 26B, 26C, and 26D and a region 26E that includes testing liquid where the color changes after reaction with the object to be analyzed. The band 26A-26D includes a different reference color, for example, purple, green, or the like. The color of the region 26E is analyzed and compared with the reference color bands to determine the property of the object to be analyzed. In some embodiments, two or more test specimens can be captured in one image and analyzed for object properties.

The terminal device 1 takes the image 23 of the test specimen 22 that has been soaked with the cooking oil that is the object to be analyzed, and acquires color information of the test specimen from the image data. In addition, if necessary the terminal device 1 determines the AV value corresponding to the color of the test specimen, by carrying out a conversion to make the color space of the taken image data coincide with the color space of the reference information stored in the memory unit 13, and carrying out a comparison of the color information of the test specimen and the reference information in a common color space (for example, the sRGB color space). Then the terminal device 1 displays the obtained AV value 24 and information indicating whether or not the AV value is within a standard range, or the like.

If the test specimen is used, there is the advantage that the object to be analyzed is not directly measured for the easy handling. Also, if the reference information is recorded in the memory unit 13, there is the advantage that the user does not have to carry a color chart. In some cases, it is possible for the user to carry reference information such as a color chart or the like, and on the spot to create a calibration curve. In some cases, a calibration using the calibration curve can be performed, for example, in the situation of unknown lighting conditions. In addition, the light emitting unit 12 with known lighting properties may be used on the spot.

In the following, three examples of the method of preparing reference information are described. If the test specimen shown in FIG. 2 is used, reference information is prepared in advance by the following methods for each of the bands A to band D, and stored in the memory unit 13.

In the first example, an image is taken of a test specimen soaked with cooking oil having a known AV value using the imaging unit 11 of the terminal device 1 by a user or by the provider of the device, and from the image data the corresponding relationship between the AV value and the color information that represents the color of the test specimen (for example, sRGB data) is obtained. In this case, the relationship of correspondence between the AV value and the color information may be obtained from a plurality of images taken of a plurality of test specimens each soaked with cooking oil having different AV values, or the relationship of correspondence may be obtained from a single image taken of the plurality of test specimens. In this example, the reference information can be prepared using the terminal device 1 only.

In the second example, an image is taken of a test specimen soaked with cooking oil having a known AV value using a separate imaging device that is different from the imaging unit 11 of the terminal device 1 by a user or by the provider of the device, and from the image data the corresponding relationship between the AV value and the color information that represents the color of the test specimen (for example, sRGB data) is obtained. If the reference information prepared by the separate imaging device is fed into the terminal device 1, then for example it is possible to increase the accuracy of the color information included in the reference information by using an imaging device with a good performance digital camera that is capable of storing with a large number of quantization bits. When a separate imaging device is used also, the relationship of correspondence between the AV value and the color information may be obtained from a plurality of images taken of a plurality of test specimens each soaked with cooking oil having different AV values, or the relationship of correspondence may be obtained from a single image taken of the plurality of test specimens.

In the third example, the optical spectra of the test specimens soaked with cooking oil having different known AV values are measured by the user or the provider of the device using a spectrophotometer, to obtain the relationship of correspondence between the AV values and the color information (for example, sRGB data) that represents the color of the test specimen from the optical spectra. In this case, for example, color information (CIEXYZ values) are calculated from the optical spectrum, and by further converting this color information into color information of the sRGB color space, the relationship of correspondence as described above can be obtained.

In more detail, the spectral reflectance for each of band A to band D is measured for a plurality of test specimens soaked with cooking oil with different degrees of oxidation (AV value). Then, the CIEXYZ values are calculated from the following equation for each of band A to band D, using the obtained spectral reflectance $R(\lambda)$, the spectral strength $H(\lambda)$ of for example a D65 light source, and the color-matching functions $x(\lambda)$, $y(\lambda)$, and $z(\lambda)$ of the XYZ color system, where $\lambda$ is the wavelength.

$X = k\int H(\lambda)R(\lambda)x(\lambda)d\lambda$ $Y = k\int H(\lambda)R(\lambda)y(\lambda)d\lambda$ $Z = k\int H(\lambda)R(\lambda)z(\lambda)d\lambda$ [Equation 1]

Here k is a standardizing coefficient.

Also, the obtained CIEXYZ values are converted into linear sRGB values in accordance with the IEC61966-2-1 standard.

$$\begin{pmatrix} R \\ G \\ B \end{pmatrix} = \begin{pmatrix} M_{11} & M_{12} & M_{13} \\ M_{21} & M_{22} & M_{23} \\ M_{31} & M_{32} & M_{33} \end{pmatrix} \begin{pmatrix} X \\ Y \\ Z \end{pmatrix}$$ [Equation 2]

Here, M11 to M33 are constants, for example, M11=3.2406, M12=−1.5372, M13=−0.4986, M21=−0.9689, M22=1.8758, M23=0.0415, M31=0.0557, M32=−0.2040, and M33=1.0570.

Then, for example, the linear sRGB values obtained are stored in the memory unit 13 as color information that represents the color of the test specimens, corresponding to the AV values.

Alternately, the linear sRGB values may be converted into non-linear sRGB values by a gamma correction in accordance with the IEC61966-2-1 standard, and the obtained non-linear sRGB values may be stored in the memory unit 13 as color information representing the color of the test specimens, corresponding to the AV values. The non-linear sRGB values obtained in this way conform to sRGB color space, so their values are the same with the sRGB values of test specimens displayed as images in the display unit 16 taken by the terminal device 1 under a D65 light source or light equal thereto. sRGB color space is one of the industry standards for color management of digital photographs, so if converted to sRGB color space, it is possible to compare the colors of test specimens with each other, regardless of the image source, such as digital photograph or video.

If an optical spectrum is used as described above, if the image taking conditions (color temperature of the lighting, relative brightness, etc.) and the color space of the image data are known, the reference information can be prepared to comply with those image taking conditions and color space by calculation. Even without taking images of test specimens under various image taking conditions in advance, it is possible to prepare reference information that is not affected by the image taking conditions. The reference information is not limited to sRGB color space, and color information in another color space may be used.

Figure 3:
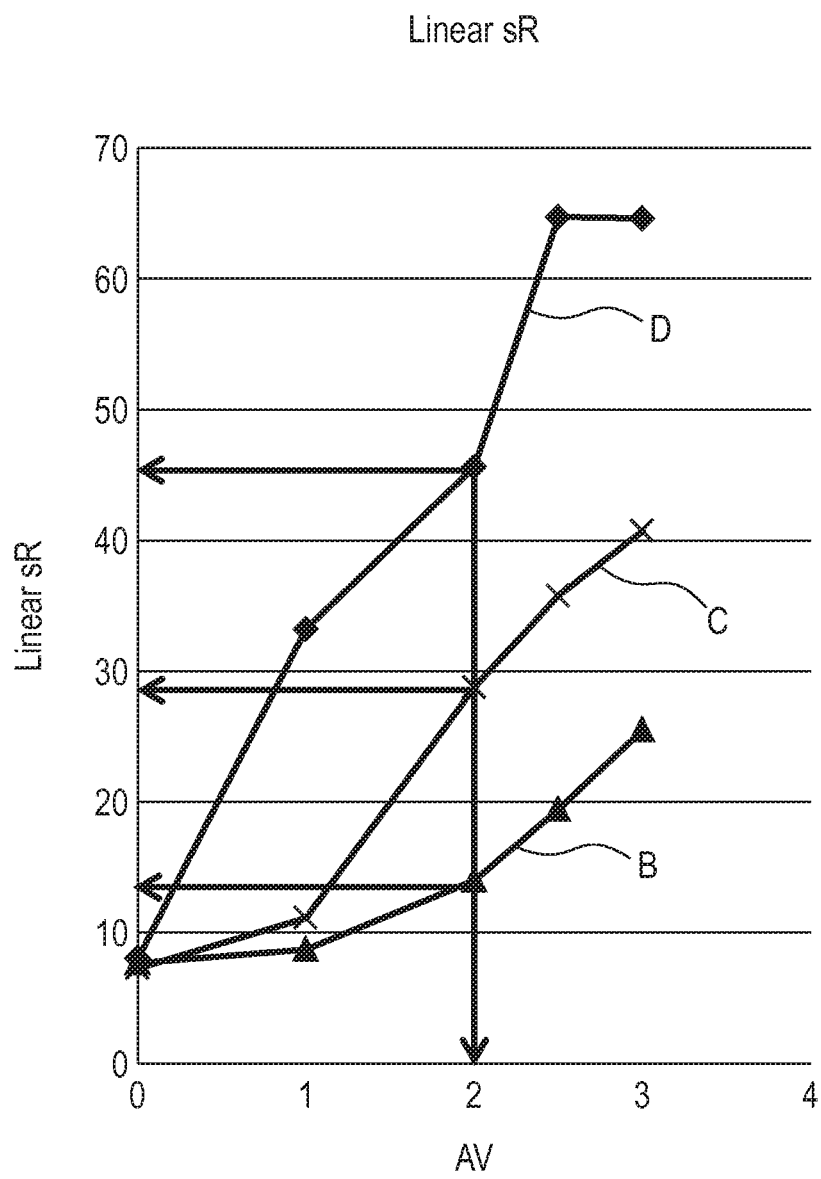
FIG. 3 is a graph showing an example of reference information.

FIG. 3 is a graph showing an example of reference information. In FIG. 3, the relationship of correspondence between the color information and the AV value for band B to band D of a test specimen obtained by one of the methods described above is shown, with the AV value on the horizontal axis and the linear sR value on the vertical axis. Although not shown on the drawing, a graph is also prepared for band A of the test specimen in the same way as for band B to band D, and in addition graphs are prepared for the sG value and the sB value in the same way as for the sR value. Also, the relationships of correspondence between the AV value and the sR value, the sG value, and the sB value are stored as reference information in the memory unit 13 for each of band A to band D of the test specimen.

Next, the various functions of the control unit 14 are described for measuring the object to be analyzed using the reference information as described above.

Figure 4:
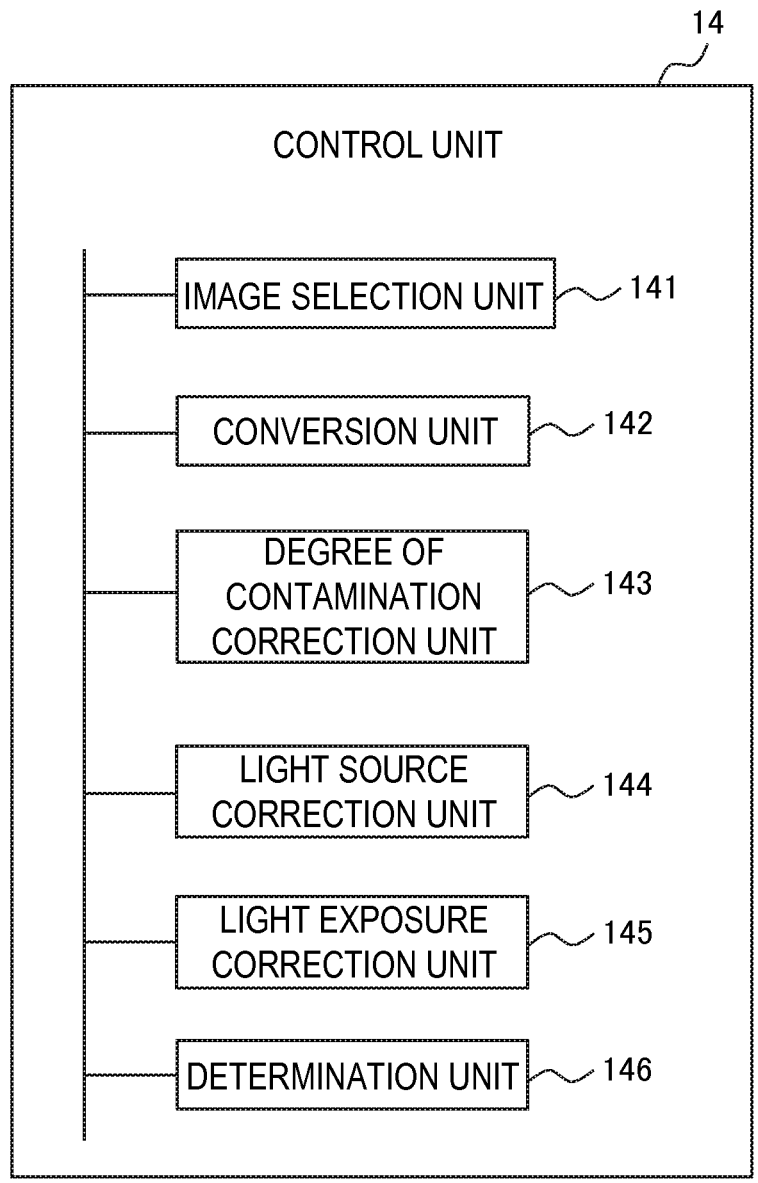
FIG. 4 is a functional block diagram of one embodiment of a control unit 14.

FIG. 4 is a functional block diagram of one embodiment of the control unit 14. The control unit 14 includes, as a functional block, an image selection unit 141, a conversion unit 142, a degree of contamination correction unit 143, a light source correction unit 144, a light exposure correction unit 145, and a determination unit 146.

The image selection unit 141 selects pixels from among images of test specimens taken by the imaging unit 11 for calculation of color information.

Figure 5:
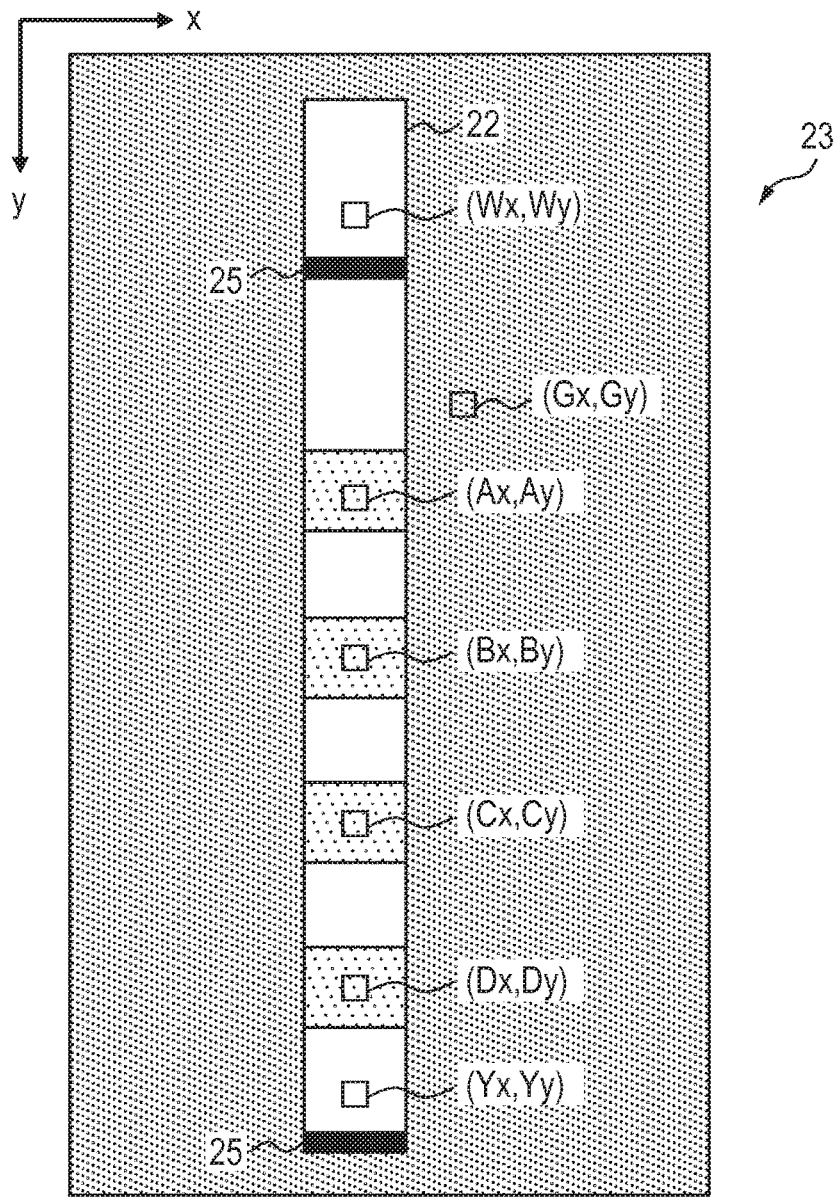
FIG. 5 shows one example of the areas of focus on an image 23 of the test specimen.

FIG. 5 show one example of the areas of focus on the image 23 of the test specimen. In FIG. 5, collections of pixels for each area of focus selected by the image selection unit 141 are indicated with small squares. The image 23 is, for example, an image taken of a test specimen 22 placed on a gray (neutral color) sheet having a reflectance of about 18%. The horizontal direction in the image 23 is the X axis, and the vertical direction is the Y axis.

In some cases, the image selection unit 141, for example, first detects the marks 25 provided in advance on the test specimen within the image 23, in order to select the pixels for the conversion unit 142 to calculate color information. Then, the image selection unit 141 detects the rectangular area with the marks 25 on the top end and the bottom end as the area that includes band A to band D. The image selection unit 141 may detect the rectangular area that includes band A to band D from the difference in density of the white areas in the test specimen apart from band A to band D, and the background gray color. Alternatively, the image selection unit 141 may detect the rectangular area by image recognition by extracting the characteristics of the test specimen 22 that includes band A to band D. Alternatively, the image selection unit 141 may detect the area of focus in accordance with an operation to specify the area of focus by a user via the operation unit 15.

In one embodiment, when the rectangular area is selected, the image selection unit 141 selects the central points (Ax, Ay), (Bx, By), (Cx, Cy), and (Dx, Dy) of band A to band D as the central pixels of band A to band D from the relative values of the positional relationship on the test specimen. Also, the image selection unit 141 selects a point (Yx, Yy) of the white portion between the mark 25 on the bottom end and the band D of the test specimen soaked with the cooking oil as the central pixel of an area of focus for correcting the effect of change of color due to contamination of the cooking oil. Also, the image selection unit 141 selects a point (Wx, Wy) of the white portion that is not soaked with cooking oil above the mark 25 on the top end of the test specimen, and a point (Gx, Gy) on the background gray sheet as central pixels of the areas of focus for correcting the color temperature of the light source and the light exposure conditions when the image was taken. In order to reduce measurement errors, the image selection unit 141 may select a plurality of pixels such as ±2 pixels or ±3 pixels in the x, y directions about each of the above points as centers to obtain 5×5 pixels or 7×7 pixels, or the like.

The conversion unit 142 makes the color space of the image data and the color space of the reference information the same by converting at least one of the color spaces, in the event that the color space of the image data of the object to be analyzed taken by the imaging unit 11 and the color space of the reference information are different. For example, the conversion unit 142 converts the color space of the image data of the object to be analyzed taken by the imaging unit 11 to the color space of the reference information, or converts the color space of the reference information to the color space of the image data. Alternatively, the conversion unit 142 may convert both the color space of the image data and the color space of the reference information to a common color space. Converting the color space of the image data to the color space of the reference information is most efficient. However, converting high accuracy reference information obtained from an optical spectrum or the like into the color space of the image data enables a higher accuracy comparison. In addition, in order to carry out the comparison at appropriate efficiency and accuracy, both the color space of the reference information and the color space of the image data may be converted to a common color space. If from the beginning the color space of the image data and the color space of the reference information are the same, the conversion unit 142 does not have to convert the color spaces.

For example, if the color space of the image data is converted to the color space of the reference information, if the RGB data of the JPEG which is the image data taken by the imaging unit 11 is not sRGB, the conversion unit 142 converts the RGB values of each of the pixels selected by the image selection unit 141 into linear sRGB values in accordance with a conversion table defined in a standard. If the image data taken by the imaging unit 11 is RAW data, the conversion unit 142 converts it to linear sRGB values using a conversion table provided by the manufacturer that manufactured the imaging unit 11.

The degree of contamination correction unit 143 determines the degree of contamination of the liquid based on the color of the test specimen that is soaked with the liquid of the object to be analyzed, and applies a correction that is predetermined in accordance with the degree of contamination to the values converted by the conversion unit 142. Cooking oil that is used frequently becomes contaminated and the color becomes brown, and if cooking oil that has been contaminated in this way is measured, the test specimen can be colored brown due to the contamination. If there is a change in color due to contamination, there is a possibility that band A to band D will be incorrectly recognized, so the degree of contamination correction unit 143 carries out a correction to remove the effect of the contamination on the sRGB values of band A to band D calculated by the conversion unit 142.

Figure 6:
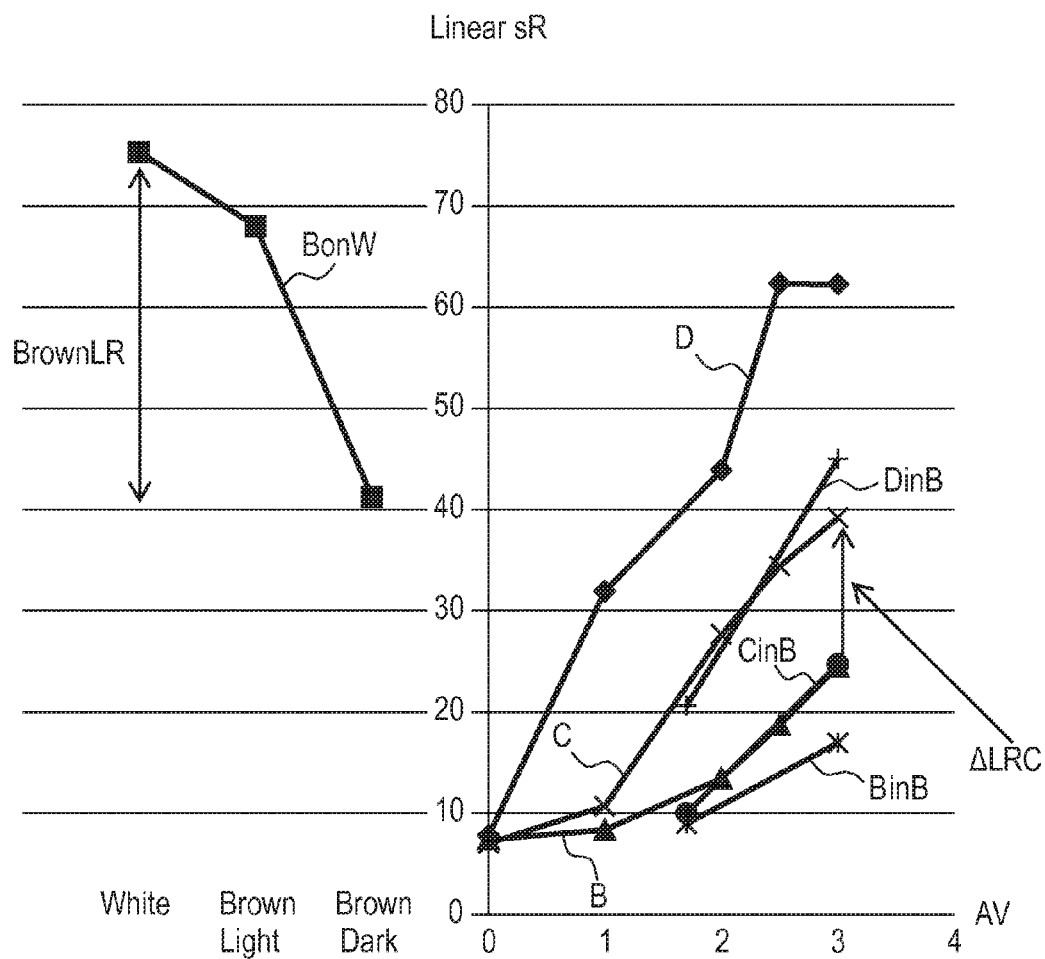
FIG. 6 is a graph for explaining the degree of contamination correction.

FIG. 6 is a graph for explaining the degree of contamination correction. The graph on the left side in FIG. 6 (BonW) shows the linear sR values at the point (Yx, Yy) of the white portion of the test specimen, for a case in which the cooking oil to be measured is not contaminated (White), the degree of contamination is low (Brown Light), and the degree of contamination is high (Brown Dark). It can be seen that as the white portion of the test specimen becomes brown due to contamination, the sR value is reduced.

The graph on the right side in FIG. 6 shows the correspondence relationship between the AV value and the linear sR value. Here graphs for the case where band B to band D are not contaminated (B, C, D) and are contaminated (BinB, CinB, DinB) are superimposed. When not contaminated, the graphs B, C, D are the same as those shown in FIG. 3. Also, for graphs BinB, CinB, DinB, the case in which the degree of contamination is the same "Brown Dark" is shown. Comparing the graphs B and BinB, C and CinB, and D and DinB, it can be seen that for each of band B to band D, the sR values are reduced by about 10 to 20 when contaminated compared with uncontaminated.

Therefore, in order to compensate for the reduction in sR value due to contamination, the degree of contamination correction unit 143 carries out a correction by adding an amount $\Delta LRC$ to the sR value calculated by the conversion unit 142. This $\Delta LRC$ is the amount of compensation corresponding to the reduction in sR value corresponding to the degree of contamination in the white portion of the test specimen BrownLR (see the left graph in FIG. 6) and the AV value.

For example, from the graph on the right side of FIG. 6, when there is no contamination ($\Delta LRC=0$) the sR value of band C LinearR is approximately represented by:

$$LinearR = 10 \times AV + 7.0$$

Therefore, when there is contamination ($\Delta LRC \neq 0$) the sR value of the band C LinearR is corrected by the degree of contamination correction unit 143 so that:

$$LinearR + \Delta LRC = 10 \times AV + 7.0$$

In this case, the AV value calculated from the sR value of the band C is calculated as follows:

$$AV = (LinearR + \Delta LRC - 7.0)/10$$

Although not shown on the drawings, the degree of contamination correction unit 143 corrects G and B of the sRGB data in the same way as described above. However, the correction by the degree of contamination correction unit 143 is not limited to addition of $\Delta LRC$, and other methods may be used. By correcting for the degree of contamination, which is background noise that produces measurement errors, in this way, the accuracy of measurement is improved.

The light source correction unit 144 calculates the color temperature of the light source based on the image data for the whole or a part of the image taken by the imaging unit 11, and applies a correction in accordance with the color temperature to the values converted by the conversion unit 142.

Figure 7:
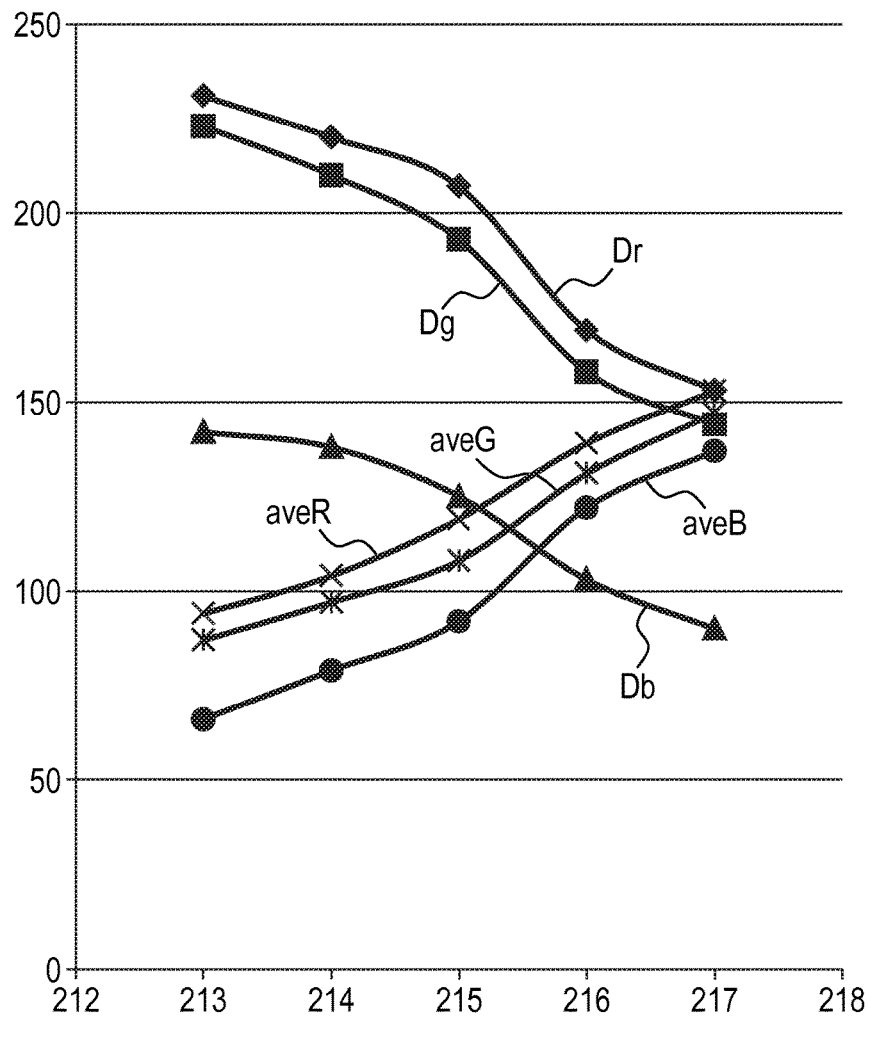
FIG. 7 is a graph for explaining the light source correction and the light exposure correction.

FIG. 7 is a graph for explaining the light source correction and the light exposure correction. In FIG. 7, the sR values, sG values, and sB values are plotted for the case where the image of the same test specimen is taken placed on five different neutral (gray) sheets with uniform but different densities. The horizontal axis corresponds to the sample number N for distinguishing the test specimen, the larger the number the brighter the sheet. The vertical axis shows the sR value, the sG value, and the sB value. The graphs Dr, Dg, and Db show the variation in the sR value, the sG value, and the sB value respectively of band D, and graphs aveR, aveG, and aveB show the variation in the average of the sR value, the sG value, and the sB value respectively.

For example, if the image of the test specimen is taken under an incandescent light source instead of a fluorescent light equivalent to D65, the sRGB values of band A to band D and the average sRGB value of the image as a whole varies due to the effect of the light source. Therefore the relationship shown in FIG. 7 is stored in the memory unit 13, and the light source correction unit 144 carries out a correction to cancel out the variation in the sRGB values due to the light source, using the relationship in FIG. 7. In this case, the light source correction unit 144 acquires at least one of the average sRGB value of the whole image taken with the test specimen placed on the gray sheet, the sRGB value of the portion of the point (Gx, Gy) of FIG. 5 (the value indicating the color of the sheet), and the sRGB value of the portion of the point (Wx, Wy) in FIG. 5 (the value indicating the white color of the test specimen). Then the light source correction unit 144 calculates the deviation from the graph in FIG. 7 for at least one of the average sRGB value of the whole image taken, the sRGB value of the sheet, and the sRGB value indicating the white color of the test specimen, and corrects the sRGB values of band A to band D obtained from the conversion unit 142 so as to just cancel out the deviation. If the background is not uniform, the light source correction unit 144 may carry out the correction based on the assumption that the overall average reflectance of the photographic subject is neutral at about 18%, and, if the background color and light source are known, the light source correction unit 144 may carry out the correction based on these. Also, if the color temperature of the lighting at the time of taking the image is recorded, the light source correction unit 144 may extract and use it.

If a visual comparison with a color chart is carried out then the observation conditions are prescribed, but if a light source correction is introduced, it is possible to carry out accurate measurement under various light sources. In addition, the color temperature of the light source can be fixed using auxiliary lighting such as a flash or the like. In particular, it is convenient if the properties of the light emitting unit 12 included in the terminal device 1 are known.

The light exposure correction unit 145 calculates the light exposure conditions of the light source based on image data for the whole or a part of the image taken by the imaging unit 11, and applies a correction to the value calculated by the conversion unit 142 in accordance with the light exposure conditions.

The graphs shown in FIG. 7 are for the case where the same test specimen is taken with uniform neutral backgrounds with different densities, but if there is no test specimen and if an automatic exposure mechanism operates, the whole image should be the same brightness (reflectance about 18%). However, when the test specimen that is almost white is placed on the gray background, this applies an error, so the brightness of the test specimen in the image varies, which affects the brightness of the test specimen.

Therefore, the light exposure correction unit 145 carries out a correction to cancel out the variation in the sRGB values due to the automatic light exposure mechanism using the relationship in FIG. 7, the same as the light source correction unit 144. In this case the light exposure correction unit 145 acquires at least one of the average sRGB value of the whole image taken with the test specimen placed on the gray sheet, the sRGB value of the point (Gx, Gy) portion of FIG. 5 (the value indicating the brightness (reflectance) of the sheet), and the sRGB value of the point (Wx, Wy) portion in FIG. 5 (the value indicating the white color of the test specimen). Then the light exposure correction unit 145 calculates the deviation from the graph in FIG. 7 for at least one of the average sRGB value of the whole image taken, the sRGB value of the sheet, and the sRGB value indicating the white color of the test specimen, and corrects the sRGB values of band A to band D obtained from the conversion unit 142 so as to just cancel out the deviation.

By correcting for differences in the background brightness level and the light exposure level with the light exposure correction unit 145, it is possible to further improve the measurement accuracy, and overcome errors due to differences in the image taking conditions.

The determination unit 146 determines the properties of the object to be analyzed (for example, the degree of oxidation of the cooking oil) by comparing the sRGB values converted by the conversion unit 142, and corrected by the degree of contamination correction unit 143, the light source correction unit 144, and the light exposure correction unit 145, with the reference information in the memory unit 13. In particular, the determination unit 146 compares the values of the color information in, for example, sRGB color space, for each of the plurality of points of band A to band D in the image of the test specimen taken by the imaging unit 11 with the reference information stored in the memory unit 13, and extracts the sRGB values of the reference information that are closest to those of band A to band D.

The determination unit 146 then determines the AV values corresponding to the extracted sRGB values, which is the degree of oxidation of the cooking oil that is the object to be analyzed. If the graph in FIG. 3 is used as reference information, then if for example the sR value of band B is 45 degrees, the sR value of band C is 28 degrees, and the sR value of band D is 13 degrees, the determination unit 146 determines that the degree of oxidation of the cooking oil that is the object to be analyzed is AV 2. The determination unit 146 causes the display unit 16 to display the AV value obtained in this way and information indicating whether or not the AV value is within a preset standard range. By the determination unit 146 determining the properties of the object to be analyzed from the measurement results at a plurality of points, it is possible to increase the accuracy of determination. For example, by using both band D and band C the dynamic range of the measurement can be increased.

Figure 8:
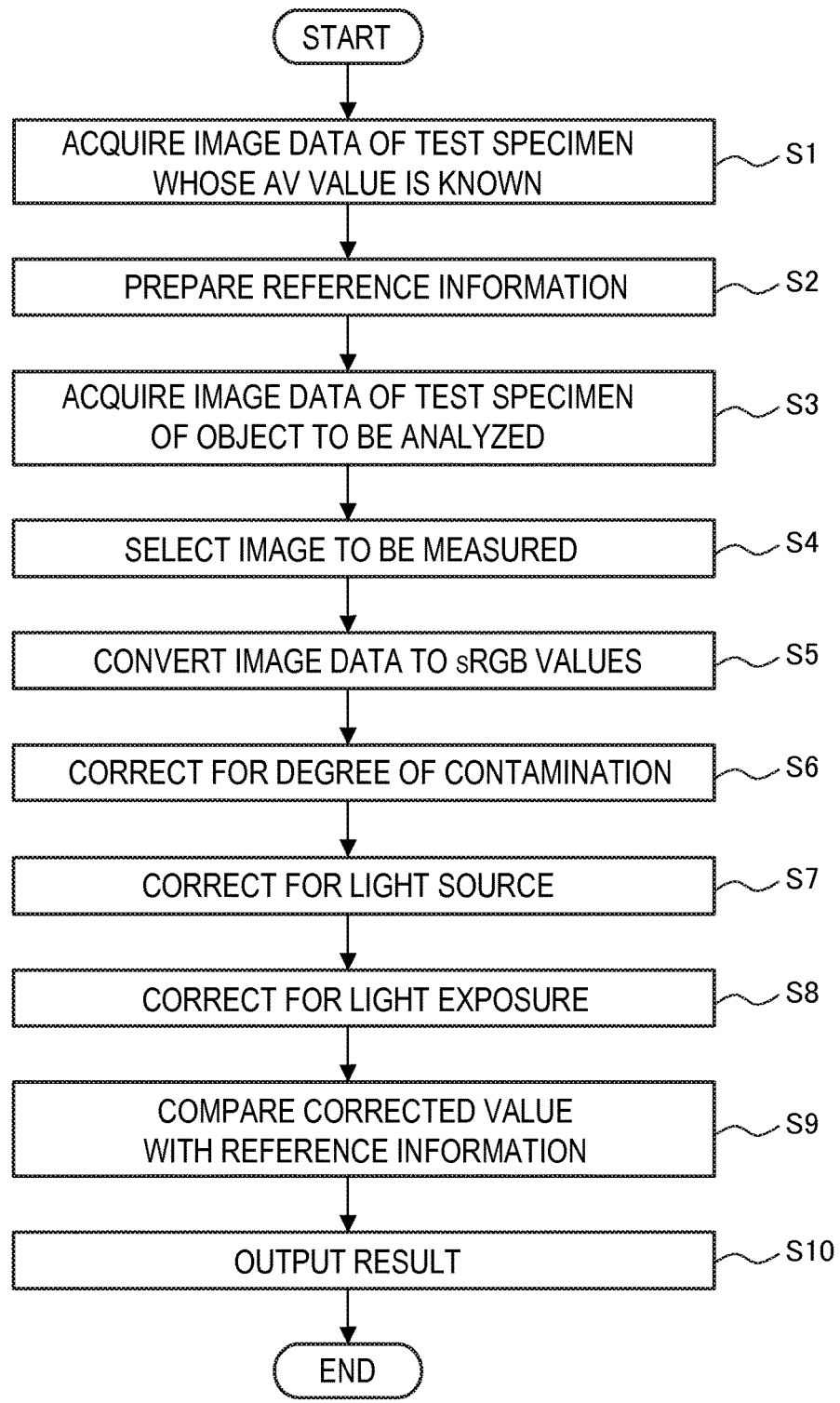
FIG. 8 is a flowchart showing an example of the colorimetric analysis process in the terminal device 1.

FIG. 8 is a flowchart showing an example of the colorimetric analysis process in the terminal device 1. The process in each block of FIG. 8 is executed by the control unit 14 in cooperation with each element of the terminal device 1 based on a program stored in the memory unit 13.

First, a plurality of test specimens that have each reacted with a plurality of cooking oils with different degrees of oxidation and known AV values is prepared. The control unit 14 acquires the plurality of image data of the test specimens taken using the imaging unit 11, and the AV value information corresponding to each of the image data is acquired from the user or from the provider of the device (step S1). Then, the control unit 14 calculates the sRGB data that represents the color of the test specimen from the image data obtained in step S1, and stores the correspondence relationship between the sRGB data and the AV values in the memory unit 13 as reference information (step S2).

When the reference information has been prepared, the control unit 14 acquires image data of a test specimen that has been soaked with the cooking oil that is the object to be analyzed taken using the imaging unit 11 (step S3). Then the image selection unit 141 detects the areas of the test specimen from the image data acquired in step S3, and selects the pixels to be measured corresponding to band A to band D of the test specimen (step S4).

Next, the conversion unit 142 carries out conversion to make the color space of the image data and the color space of the reference information the same. In this case, for example the conversion unit 142 converts the image data corresponding to the pixels of band A to band D selected by the image selection unit 141 in the step S4 to values (sRGB values) of the sRGB color space, which is the same as that of the reference information (step S5). Alternatively, the conversion unit 142 may convert the color space of the reference information to the color space of the image data, or convert both the color space of the image data and the color space of the reference information to a common color space. If from the beginning the color space of the image data and the color space of the reference information are the same, step S5 may be omitted.

The values obtained in step S5 include the effect of contamination of the cooking oil that is the object to be analyzed, and include the effect of differences in the color temperature of the light source. Therefore, correction is carried out by the degree of contamination correction unit 143 to remove the effect of the degree of contamination (step S6), correction is carried out by the light source correction unit 144 for the color temperature of the light source (step S7), and correction for the light exposure conditions is carried out by the light exposure correction unit 145 (in particular, correction of errors in the brightness due to an automatic light exposure mechanism and so on) (step S8).

Next, the determination unit 146 compares the sRGB values corrected in steps S6 to S8 with the reference information in the memory unit 13, and extracts from the reference information that which is closest to the corrected sRGB values (step S9). Then the determination unit 146 causes the display unit 16 to display the AV value corresponding to the sRGB values extracted in step S9 as the determination result (step S10). In step S10, determination information indicating whether or not the determined AV value is within a predetermined standard range may also be output. This completes the colorimetric analysis process by the terminal device 1.

In step S1, the control unit 14 may acquire the image data taken by a separate imaging device that is different from the imaging unit 11, as described above. Alternatively, instead of acquiring the image data in step S1, the control unit 14 may acquire optical spectrum data of a plurality of test specimens that were separately measured, or color information calculated from them. If optical spectrum data is acquired, in step S2 the control unit 14 prepares the reference information by obtaining the CIE XYZ values from the optical spectrum data, and converting it to, for example, sRGB data.

As described above, according to the terminal device 1, it is possible to carry out colorimetric analysis with higher objectivity than visual judgment using a color chart, using a general purpose imaging device and a general purpose information processing device, without a dedicated analysis device. If all the necessary hardware is incorporated into a hand held instrument, it is possible to realize the terminal device 1 by just installing a program that realizes the function of the control unit 14.

Figure 9:
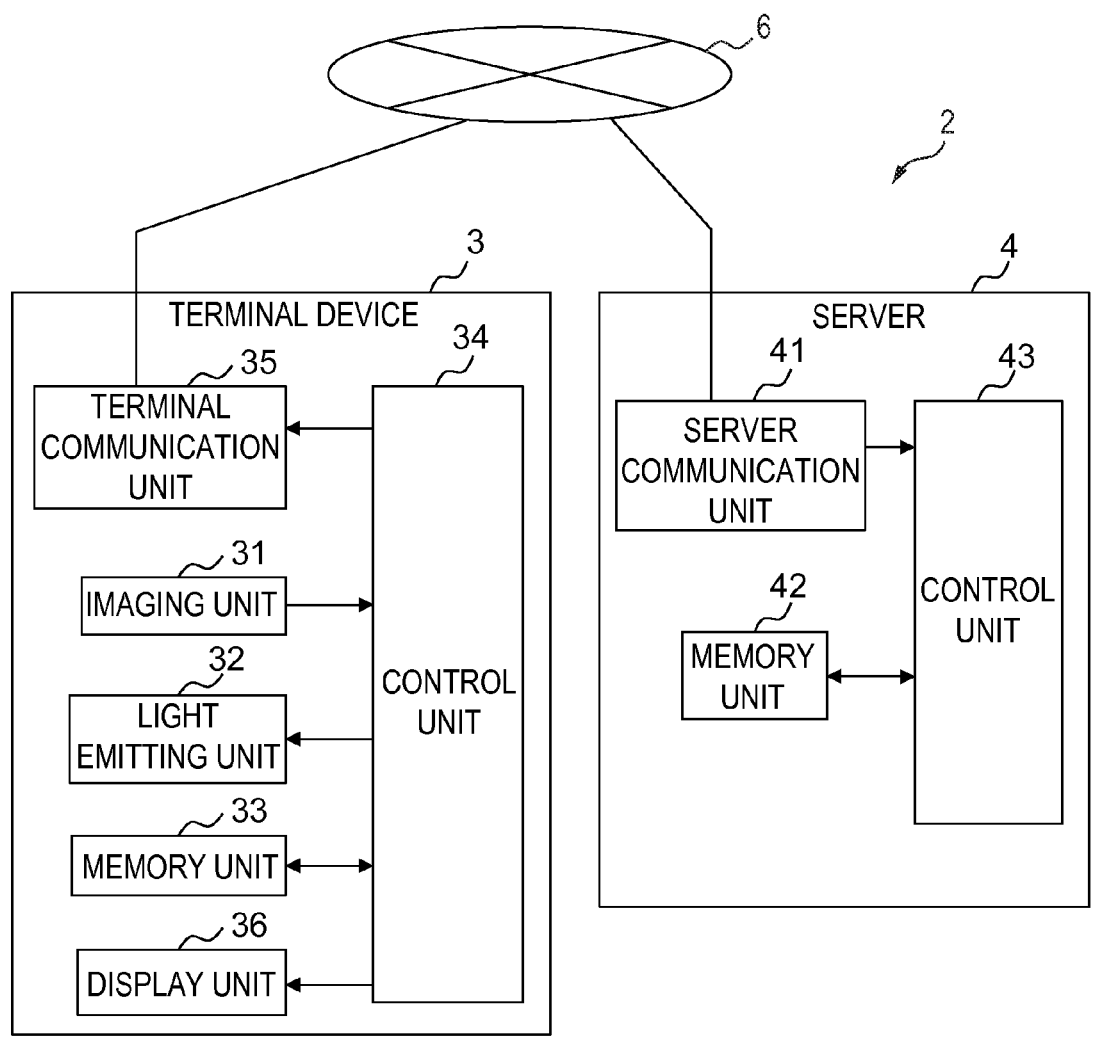
FIG. 9 is a schematic configuration of one embodiment of a communication system 2.

FIG. 9 is a schematic configuration of one embodiment of a communication system 2. The communication system 2 is a system for colorimetric analysis, and includes a terminal device 3 and a server 4 that can communicate with each other. These devices are connected to each other via a wired or wireless communication network 6.

The terminal device 3 includes an imaging unit 31, a light emitting unit 32, a memory unit 33, a control unit 34, a terminal communication unit 35, and a display unit 36. The imaging unit 31 takes an image of the object to be analyzed, and obtains image data of the test specimen in the format of RAW (DNG) data, JPEG (JFIF) data, or RGB data, or the like. The light emitting unit 32 if necessary emits light when an image is being taken by the imaging unit 31. The memory unit 33 stores the image data taken by the imaging unit 31, data necessary for operation of the terminal device 3, and so on. The control unit 34 includes a CPU, RAM, ROM, and so on, and controls the operation of the terminal device 3. The terminal communication unit 35 transmits image data taken by the imaging unit 31 to the server 4, and receives from the server 4 the determination results of the image data. The display unit 36 displays the determination results received from the server 4.

The server 4 includes a server communication unit 41, a memory unit 42, and a control unit 43. The server communication unit 41 receives image data from the terminal device 3, and transmits the image data determination results to the terminal device 3. The memory unit 42 stores image data received from the terminal device 3, imaging information, data required for operation of the server 4, and so on. In particular, the memory unit 42 stores color information of an object to be analyzed in accordance with the properties of the object to be analyzed as reference information. The control unit 43 includes a CPU, RAM, ROM, and so on, and controls functions the same as the control unit 14 of the terminal device 1. In other words, if the color space of the image data of the test specimen received from the terminal device 3 and the color space of the reference information are different, the control unit 43 makes the color space of the image data and the color space of the reference information the same by converting the color space of at least one of them. Also, the control unit 43 determines the properties of the object to be analyzed by comparing color information of the image data and the color information of the reference information of the memory unit 42 in a common color space.

In this way, taking the image of the test specimen and displaying the determination results, and determining the properties of the object to be analyzed may be carried out in separate devices. If a high speed and high capacity server 4 is used, it is possible to carry out highly accurate analysis by complex image processing, and joint operation with separate databases is also easy. The communication system 2 may further include a separate display device, so the determination results of the server 4 may be displayed in a device that is separate from the terminal device 3.

In the description above, an example was described in which a liquid object to be analyzed was measured using the test specimen, but the object to be analyzed is not limited to a liquid, and it may be a gas or a powder. Alternatively, the object to be analyzed may be a liquid crystal thermometer, an impact sensor, a color temperature meter, a printed material (with the purpose of control of color unevenness), a color difference meter, and so on, provided the color changes in accordance with the change of state there is no limitation to the examples described.

Also, a computer program for realizing each of the functions of the conversion unit on a computer may be provided stored on a non-transitory storage medium such as a magnetic storage medium or an optical storage medium that can be read by a computer.

Figure 10:
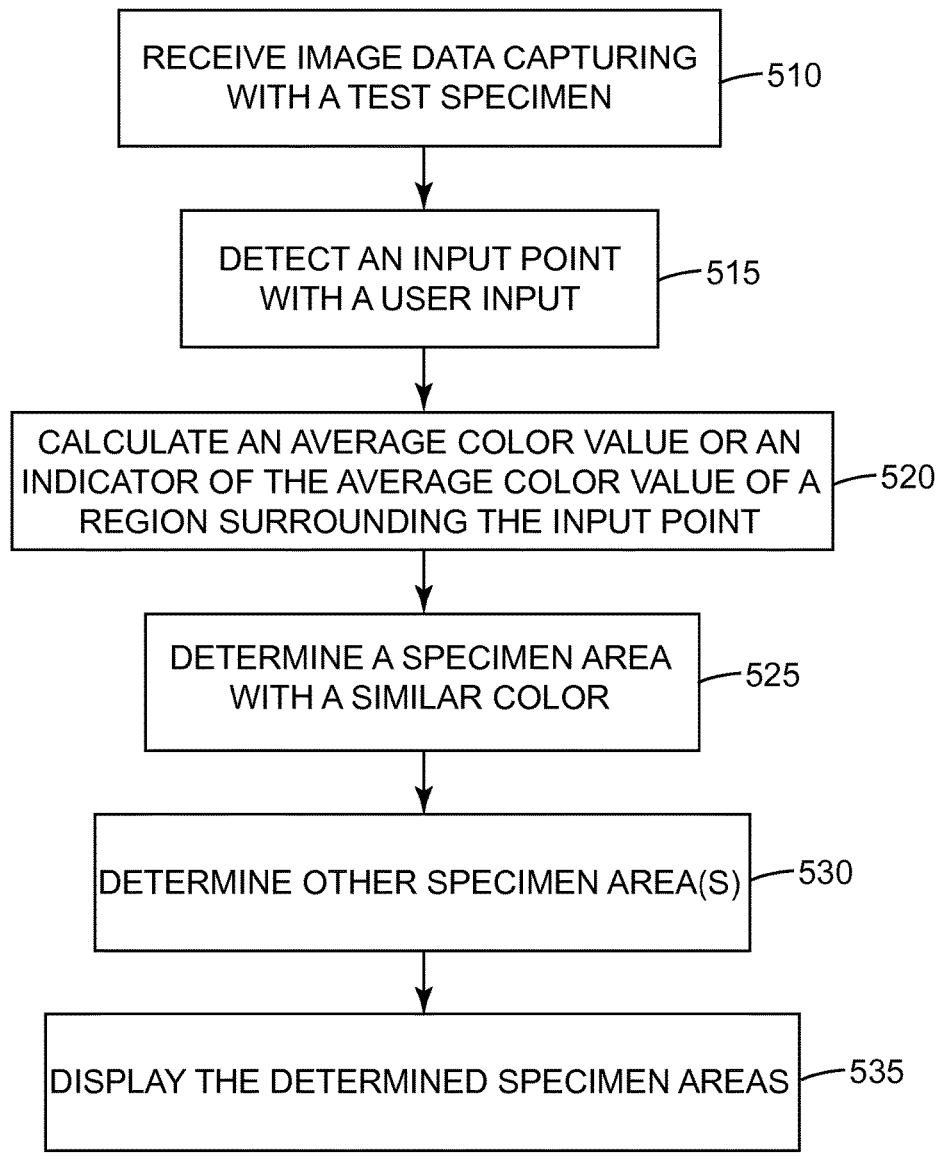
FIG. 10 is a flowchart showing another example of the colorimetric analysis process.

FIG. 10 is a flowchart showing another example of the colorimetric analysis process implemented by an analysis apparatus including a device or a system, for example, implemented by the terminal device 1 or communication system 2 described herein. In some embodiments, the process in each block of FIG. 10 is executed by the control unit 14 in cooperation with each element of the terminal device 1 based on a program stored in the memory unit 13. First, the analysis apparatus receives image data capturing with a test specimen (step 510). The analysis apparatus detect an input point with a user input (step 515). In some cases, a touch screen is used, and the user input is received via touch screen. Next, the analysis apparatus calculates an average color value or an indicator of the average color value of a region surrounding the input point using the image data (step 520). For example, the region is a 3×3 square surrounding the input point and the average color value is the average sRGB value of the nine points within the region. The analysis apparatus can determine a specimen area with similar color using the average color value and/or the region (step 525). For example, with an input point within band D or band 26E illustrated in FIG. 2, the entire band D can be detected. Optionally, in some cases, the analysis apparatus determines other specimen area(s) (e.g., band A, band B, band 26A, band 26D, etc.) (step 530). As another optional step, the analysis apparatus displays the determined specimen areas (step 535).

EXEMPLARY EMBODIMENTS

Item 1. A device for performing colorimetric analysis, comprising:

an imaging unit that takes images of an object to be analyzed;

a memory unit that stores reference information of color information of the object to be analyzed in accordance with the properties of the object to be analyzed;

a conversion unit that, when the color space of the image data of the object to be analyzed taken by the imaging unit and the color space of the reference information are different, makes the color space of the image data and the color space of the reference information the same by converting at least one of the color spaces;

a determination unit that determines the properties of the object to be analyzed by comparing the color information of the image data and the color information of the reference information in a common color space; and a display unit that displays the determination results of the determination unit.

Item 2. The device according to Item 1, wherein when the color space of the image data and the color space of the reference information are different, the conversion unit converts the color information of the reference information to values of color information in the color space of the image data.

Item 3. The device according to Item 1, wherein when the color space of the image data and the color space of the reference information are different, the conversion unit converts the color information of the image data to values of color information in the color space of the reference information.

Item 4. The device according to Item 1, wherein when the color space of the image data and the color space of the reference information are different, the conversion unit converts the color information of the color space of the image data and the color information of the color space of the reference information to values of color information in a common color space.

Item 5. The device according to any one of Items 1 to 4, wherein the reference information is prepared in advance using image data taken by the imaging unit of the object to be analyzed having different known properties.

Item 6. The device according to any one of Items 1 to 4, wherein the reference information is prepared in advance using image data taken by an imaging device that is different from the imaging unit of the object to be analyzed having different known properties.

Item 7. The device according to any one of Items 1 to 4, wherein the reference information is prepared by obtaining in advance the optical spectra of the object to be analyzed with known properties, and converting color information calculated from the optical spectra into color information in the color space of the image data.

Item 8. The device according to any one of Items 1 to 7, wherein the imaging unit takes an image of a test specimen that has contacted the object to be analyzed, and wherein the memory unit stores color information that represents the color of the test specimen in accordance with the properties of the object to be analyzed, as reference information.

Item 9. The device according to Item 8, wherein the object to be analyzed is a liquid;

the imaging unit takes an image of a test specimen that has been soaked with the liquid to be analyzed; and the memory unit stores color information that represents the color of the test specimen in accordance with the properties of the liquid, as reference information.

Item 10. The device according to Item 9, further comprising a degree of contamination correction unit that determines the degree of contamination of the liquid based on the color of the test specimen soaked with the liquid, and applies a correction that is predetermined in accordance with the degree of contamination to the value converted by the conversion unit;

wherein the determination unit compares the value corrected by the degree of contamination correction unit with the reference information.

Item 11. The device according to any one of Items 1 to 10, further comprising a light source correction unit that calculates the color temperature of the light source based on the whole or a part of the image data of the image taken by the imaging unit, and applies a correction in accordance with the color temperature to the value converted by the conversion unit;

wherein the determination unit compares the value corrected by the light source correction unit with the reference information.

Item 12. The device according to any one of Items 1 to 11, further comprising a light exposure correction unit that calculates the light exposure conditions of the light source based on the whole or a part of the image data of the image taken by the imaging unit, and applies a correction in accordance with the light exposure conditions to the value converted by the conversion unit;

wherein the determination unit compares the value corrected by the light exposure correction unit with the reference information.

Item 13. The device according to any one of Items 1 to 12, wherein the determination unit determines the properties of the object to be analyzed by comparing the values of the color information in the common color space for a plurality of points in the image taken by the imaging unit with the reference information.

Item 14. A system for performing colorimetric analysis comprising a terminal device and a server which can communicate with each other, wherein:

the terminal device includes:

an imaging unit that takes images of an object to be analyzed;

a terminal communication unit that transmits image data of the object to be analyzed taken by the imaging unit to the server, and receives determination results for the image data from the server; and a display unit that displays the determination results; and the server includes:

a memory unit that that stores reference information of color information of the object to be analyzed in accordance with the properties of the object to be analyzed;

a conversion unit that, when the color space of the image data of the object to be analyzed received from the terminal device and the color space of the reference information are different, makes the color space of the image data and the color space of the reference information the same, by converting at least one of the color spaces;

a determination unit that determines the properties of the object to be analyzed by comparing the color information of the image data and the color information of the reference information in a common color space; and a server communication unit that receives the image data from the terminal device and transmits the determination results to the terminal device.

Item 15. A program executed on a computer that includes a memory unit that stores reference information of color information of the object to be analyzed in accordance with the properties of the object to be analyzed, the program comprising:

acquiring image data of the object to be analyzed taken by an imaging device;

making the color space of the image data and the color space of the reference information the same, by converting at least one of the color spaces when the color space of the image data of the object to be analyzed taken by the imaging device and the color space of the reference information are different;

determining the properties of the object to be analyzed by comparing the color information of the image data and the color information of the reference information in a common color space; and preparing display data for displaying the determination results of the properties of the object to be analyzed.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices falling within the spirit and scope of the invention as defined by the appended claims and their equivalents.

What is claimed is:

1. A device for performing colorimetric analysis, comprising:
   an imaging unit configured to take images of an object to be analyzed;
   a memory unit configured store reference information of color information of the object to be analyzed in accordance with the properties of the object to be analyzed;
   a conversion unit configured to convert at least one of the color space of the image data and the color space of the reference information to a common color space, if the color space of the image data of the object to be analyzed taken by the imaging unit and the color space of the reference information are different from each other;
   a determination unit configured to determine the properties of the object to be analyzed by comparing the color information of the image data and the color information of the reference information in the common color space;
   a display unit that displays the determination results of the determination unit,
   wherein the object to be analyzed is a liquid; wherein the imaging unit takes an image of a test specimen that has been soaked with the object to be analyzed; and wherein the memory unit stores color information that represents the color of the test specimen in accordance with the properties of the liquid, as reference information,
   a degree of contamination correction unit that determines the degree of contamination of the liquid based on the color of the test specimen soaked with the object, and applies a correction that is predetermined in accordance with the degree of contamination to the value converted by the conversion unit, wherein the determination unit compares the value corrected by the degree of contamination correction unit with the reference information; and
   a light source correction unit that calculates the color temperature of the light source based on the whole or a part of the image data of the image taken by the imaging unit, and applies a correction in accordance with the color temperature to the value converted by the conversion unit, wherein the determination unit compares the value corrected by the light source correction unit with the reference information.

2. The device according to claim 1, wherein if the color space of the image data and the color space of the reference information are different, the conversion unit converts the color information of the reference information to values of color information in the color space of the image data.

3. The device according to claim 1, wherein when the color space of the image data and the color space of the reference information are different, the conversion unit converts the color information of the image data to values of color information in the color space of the reference information.

4. The device according to claim 1, wherein when the color space of the image data and the color space of the reference information are different, the conversion unit converts the color information of the color space of the image data and the color information of the color space of the reference information to values of color information in a common color space.

5. The device according to claim 1, wherein the reference information is prepared in advance using image data taken by the imaging unit of the object to be analyzed having different known properties.

6. The device according to claim 1, wherein the reference information is prepared in advance using image data taken by an imaging device that is different from the imaging unit of the object to be analyzed having different known properties.

7. The device according to claim 1, wherein the reference information is prepared by obtaining in advance the optical spectra of the object to be analyzed with known properties, and converting color information calculated from the optical spectra into color information in the color space of the image data.

8. The device according to claim 1, further comprising:
   a light exposure correction unit that calculates the light exposure conditions of the light source based on the whole or a part of the image data of the image taken by the imaging unit, and applies a correction in accordance with the light exposure conditions to the value converted by the conversion unit;
   wherein the determination unit compares the value corrected by the light exposure correction unit with the reference information.

9. The device according to claim 1, wherein the determination unit determines the properties of the object to be analyzed by comparing the values of the color information in the common color space for a plurality of points in the image taken by the imaging unit with the reference information.

10. A system for performing colorimetric analysis comprising a terminal device and a server which can communicate with each other, wherein:
    the terminal device includes:
    an imaging unit that takes images of an object to be analyzed;
    a terminal communication unit that transmits image data of the object to be analyzed taken by the imaging unit to the server, and receives determination results for the image data from the server; and a display unit that displays the determination results; and
the server includes:
a memory unit that that stores reference information of color information of the object to be analyzed in accordance with the properties of the object to be analyzed;
a conversion unit configured to convert at least one of the color space of the image data and the color space of the reference information to a common color space, if the color space of the image data of the object to be analyzed taken by the imaging unit and the color space of the reference information are different from each other;
a determination unit that determines the properties of the object to be analyzed by comparing the color information of the image data and the color information of the reference information in a common color space;
a server communication unit that receives the image data from the terminal device and transmits the determination results to the terminal device,
wherein the object to be analyzed is a liquid; wherein the imaging unit takes an image of a test specimen that has been soaked with the object to be analyzed; and wherein the memory unit stores color information that represents the color of the test specimen in accordance with the properties of the liquid, as reference information,
a degree of contamination correction unit that determines the degree of contamination of the liquid based on the color of the test specimen soaked with the object, and applies a correction that is predetermined in accordance with the degree of contamination to the value converted by the conversion unit, wherein the determination unit compares the value corrected by the degree of contamination correction unit with the reference information; and
a light source correction unit that calculates the color temperature of the light source based on the whole or a part of the image data of the image taken by the imaging unit, and applies a correction in accordance with the color temperature to the value converted by the conversion unit, wherein the determination unit compares the value corrected by the light source correction unit with the reference information.

11. A non-transitory computer-readable medium comprising instructions, when executed on a computer that includes a memory unit that stores reference information of color information of the object to be analyzed in accordance with the properties of the object to be analyzed, cause the computer to perform a method, the method comprising:
acquiring image data of the object to be analyzed taken by an imaging device, the object being a liquid, wherein the imaging device takes an image of a test specimen that has been soaked with the object to be analyzed;
storing color information that represents the color of the test specimen in accordance with the properties of the liquid, as reference information;
converting at least one of the color space of the image data and the color space of the reference information to a common color space, if the color space of the image data of the object to be analyzed taken by the imaging unit and the color space of the reference information are different from each other;
determining the degree of contamination of the liquid based on the color of the test specimen soaked with the object;
applying a correction that is predetermined in accordance with the degree of contamination to the converted value;
comparing the value corrected in accordance with the degree of contamination with the reference information;
calculating the color temperature of the light source based on the whole or a part of the image data of the image taken by the imaging device;
applying a correction in accordance with the color temperature to the converted value;
comparing the value corrected in accordance with the color temperature with the reference information;
determining the properties of the object to be analyzed by comparing the color information of the image data and the color information of the reference information in a common color space; and
preparing display data for displaying the determination results of the properties of the object to be analyzed.

* * * * *